United States Patent
Caponetti et al.

(10) Patent No.: US 10,226,421 B2
(45) Date of Patent: *Mar. 12, 2019

(54) PHARMACEUTICAL COMPOSITION CONTAINING BUDESONIDE AND FORMOTEROL

(71) Applicant: Zambon S.P.A., Bresso (IT)

(72) Inventors: Giovanni Caponetti, Piacenza (IT); Loretta Maggi, Piacenza (IT); Marco Sardina, Gerenzano (IT); Franco Castegini, Vicenza (IT); Gianluigi Faiella, Verona (IT); Daniela Rebolini, Mantova (IT)

(73) Assignee: Zambon S.P.A., Bresso (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/783,533

(22) PCT Filed: Apr. 9, 2014

(86) PCT No.: PCT/EP2014/057209
§ 371 (c)(1),
(2) Date: Oct. 9, 2015

(87) PCT Pub. No.: WO2014/167028
PCT Pub. Date: Oct. 16, 2014

(65) Prior Publication Data
US 2016/0081925 A1 Mar. 24, 2016

(30) Foreign Application Priority Data
Apr. 10, 2013 (IT) .............................. MI2013A0571

(51) Int. Cl.
| | | |
|---|---|---|
| A61K 9/00 | (2006.01) | |
| A61K 9/16 | (2006.01) | |
| A61K 31/167 | (2006.01) | |
| A61K 31/58 | (2006.01) | |

(52) U.S. Cl.
CPC .......... *A61K 9/0075* (2013.01); *A61K 9/1617* (2013.01); *A61K 9/1623* (2013.01); *A61K 31/167* (2013.01); *A61K 31/58* (2013.01)

(58) Field of Classification Search
None
See application file for complete search history.

(56) References Cited

U.S. PATENT DOCUMENTS

| 2001/0049396 A1 | 12/2001 | Ekstrom |
| 2008/0226736 A1 | 9/2008 | Caponetti et al. |

FOREIGN PATENT DOCUMENTS

| WO | WO-98/15280 A1 | | 4/1998 |
| WO | WO-00/35441 A2 | | 6/2000 |
| WO | WO200051591 | * | 9/2000 |
| WO | WO-02/00197 A1 | | 1/2002 |
| WO | WO-2004/093848 A2 | | 11/2004 |

OTHER PUBLICATIONS

Tajber et al., Spray drying of budesonide, formoterol fumarate and their composites—I. Physicochemical characterisation, International Journal of Pharmaceutics 367 (2009) 79-85.*
Szafranski et al., Efficacy and safety of budesonide/formoterol in the management of chronic obstructive pulmonary disease, Eur Respir J 2003; 21: 74-81.*

* cited by examiner

*Primary Examiner* — Jennifer A Berrios
(74) *Attorney, Agent, or Firm* — Polsinelli PC

(57) ABSTRACT

The present invention relates to drug formulations in dry powder form for administration by inhalation and indicated for the treatment of obstructive airway syndromes such as asthma and chronic obstructive pulmonary disease (COPD). In particular, the invention relates to an inhalable pharmaceutical composition comprising a first powder consisting of budesonide, or one of its pharmaceutically allowable salts, in a quantity greater than 5% w/w of said first powder, leucine in a quantity in the range of 5 to 70% w/w of said first powder, and lactose in a quantity in the range of 20 to 90% w/w of said first powder; a second powder consisting of formoterol, or one of its pharmaceutically allowable salts, in a quantity greater than 1% w/w of said second powder, leucine in a quantity in the range of 5 to 70% w/w of said second powder, and lactose in a quantity in the range of 20 to 90% w/w of said second powder; and a third powder consisting of leucine in a quantity in the range of 5 to 70% w/w of said third powder, and lactose in a quantity in the range of 20 to 90% w/w of said third powder. Said composition has a fine particle fraction (FPF) greater than 60% and a delivered fraction (DF) greater than 90%.

19 Claims, No Drawings

PHARMACEUTICAL COMPOSITION CONTAINING BUDESONIDE AND FORMOTEROL

CROSS REFERENCE TO RELATED APPLICATIONS

This application is a National Phase filing under 35 U.S.C. § 371 of PCT/EP2014/057209 filed on Apr. 9, 2014; and this application claims priority to Application No. MI2013A000571 filed in Italy on Apr. 10, 2013. The entire contents of each application are hereby incorporated by reference.

The present invention relates to drug formulations in the form of a dry powder for administration by inhalation, indicated for the treatment of obstructive respiratory syndromes such as asthma and chronic obstructive pulmonary disease (COPD). For the treatment of asthma, in particular, these formulations are indicated for use both as maintenance therapy and on demand.

Inhalation therapy with aerosol preparations is used to deliver active ingredients within the respiratory tract, to the mucosal, tracheal and bronchial sites. The term 'aerosol' describes a nebulised liquid preparation consisting of fine particles carried by a gas (normally air) to the site where their therapeutic action is required. When this site of action involves the alveoli and bronchioles, the drug must be dispersed in the form of droplets or particles smaller than 5.0 μm in aerodynamic diameter. Larger particles are more appropriate when the target is the pharyngeal region.

Conditions suitable for such treatments include bronchospasm, poor airway compliance, mucosal oedema, lung infections, and the like. Drugs are currently administered to the lower lungs by delivering them with the aid of inhaler devices, such as:
- nebulisers, in which case the drug is dissolved or dispersed in a suspension and carried inside the lung in the form of fine nebulised droplets;
- inhaler devices for use with powders, which can deliver the drug contained in the inhaler in the form of micronised dry particles;
- pressurised inhalers, in which case the drug (again in the form of droplets of solution or suspension) is carried inside the lower lung by an inert gas that expands rapidly in air delivered from a pressurised bottle.

In all these cases, technological difficulties have been encountered in the preparation of efficient and effective products, meaning that the administration of the drugs by inhalation is still restricted today in some situations and some types of patient.

From a technical standpoint, an ideal inhalable product should enable its administration to patients using various modes of administration because the above-described inhaler devices are generally appropriate for different types of patient and different drug administration situations. Generally speaking, therapy with a nebuliser is used mainly for the very elderly or for paediatric patients, while drugs delivered in the form of inhaled powders or using pressurised inhalers are more often used by adult or adolescent patients. The use of nebulisers is still considered valid, however, because patients inhale the drug in resting conditions and without forcing their inspiratory action, whereas this becomes necessary in the case of drugs formulated as inhalable powders.

When a pressurised inhaler is used, on the other hand, administering the product involves coordinating the inspiratory the action with the operation of the inhaler device to avoid the particles it deliver impacting against the throat instead of reaching the lower lungs.

From the therapeutic standpoint, patients may be restricted by the fact that they cannot use the same drug in different conditions, e.g. at home, at work, while travelling, or in the event of an emergency. In these various situations, it may be that a given patient has to use different drugs and/or formulations containing different active ingredients.

Among the most obvious difficulties encountered in the formulation of drugs for use in the development of inhalable products, the most important concerns the chemical stability vis-à-vis atmospheric agents, which can cause a rapid degradation of inhalable preparations and a consequently short life of the ingredients they contain.

The stability of a drug formulated for inhalation is particularly important in relation to the fact that it has to be distributable over the whole surface of the lung, including the alveoli (deep inside the lung), while maintaining its physical characteristics. There is also the fact that there is an extremely limited number of excipients currently approved for administration by inhalation, and consequently having no toxicity in relation to lung tissue.

There are dry powders for inhalation described in the literature that are readily dispersible in air thanks to their low density. These powders are usually formulated with a high content of phospholipids, and particularly of dipalmitoyl-phosphatidylcholine (DPPC).

A powder of this type is described in the patent application US2005/0074498 A1, relating to low-density particles with a hollow morphology obtained by spray drying and using surfactants consisting of phospholipids in combination with a blowing agent. The hollow structure is described as resulting from a precise combination of blowing agent and phospholipid surfactant. There are no reports of such a morphology being obtained without phospholipids. Using phospholipids as surfactants determines the principal characteristics of the end product, and especially its stability and sensitivity to atmospheric agents, which will be particularly influenced by humidity in the case in point. The patent literature (US 2001/0036481 A1) also reports the glass-rubber transition temperatures (Tg) for phospholipids in the presence of a humidity of 41° C. for DPPC, 55° C. for distearoyl-phosphatidylcholine (DSPC), and 63° C. for dipalmitoyl-phosphatidylethanolamine (DPPE), which are the three most compatible phospholipids in terms of their administration in the lung.

The transition temperature (Tg) is defined as the temperature needed to induce a change in the lipids' physical state from the orderly gel phase (in which the hydrocarbon chains are completely flat and closely packed) to a disorderly liquid-crystalline phase (in which the hydrocarbon chains are randomly oriented and fluid). These Tg values are all below the Tg characteristic of amorphous lactose. It is common knowledge that transition is easier the closer the Tg comes to the ambient temperature at which a preparation is stored. It is also well known that, in a system in which the principal excipient is fluid, not compact, the molecular mobility of the components is very high with a consequent propensity for different chemical reactions to take place and for active ingredients to undergo degradation.

Using phospholipids to make porous particles for administering by inhalation consequently does not seem to be supported by reasonable scientific considerations concerning the product's long-term stability.

In addition to the application as a powder for inhalation, the patent application in question also describes an application of the same particles in an inhaler device with a propellant. Such an administration method would be impossible using a conventional nebuliser and dispersing the particles in water or an aqueous solution, given the materials' incompatibility with water and their tendency to float on the surface of a fluid and then slowly dissolve within it. The concept of "high porosity" or "low density" was used to mean substantially the same thing in the above-mentioned patent applications. In particular, the term 'density' is used referring not to the particles' absolute density—because, measured with a helium pycnometer, this would identify the density of the solid materials comprising the powder and the particles according to the equation:

$$\rho = \text{weight/volume (g/cc)}$$

but to the particles' apparent density (in some publications by other authors this is called "envelope density"), taking into consideration their overall volume.

Given the technical difficulty of measuring this overall volume for each single particle, the above-mentioned patent applications referred to parameters of the powder's volume (and subsequently of its density) as the volume 'as poured' (or bulk volume) and after settling (or tapped volume), which give an extremely imprecise indication of the density of the particles comprising a powder.

The patent application CA2536319 describes a pharmaceutical composition obtained by spray drying, in which the humidity content is lower than 1%. According to the description, such a low humidity content is functional to the stability of the composition, since a water content in the powder higher than 1% would lead to degradation of the pharmacologically active ingredients with a consequent loss of the preparation's efficacy. To reduce the humidity level, the preparation contains a large quantity of mannitol, which considerably interferes with the physical characteristics of the powder, however, increasing the size of the particles and reducing the dose of powder delivered by the mouthpiece of the inhaler device used (i.e. the inhaled dose).

The problem of obtaining inhalable powders with a high dispersibility has been overcome by engineering particles that contain the drug as thoroughly dispersed as possible. In short, the technique used to do so involves preparing essentially fine particles (with a mean geometrical diameter greater than 4.0 μm) consisting of small quantities of active ingredient dispersed down to molecular level in an appropriate matrix of excipients capable of ensuring the formation of a gross, low-density particle using the spray drying method.

This formulation method necessitates the use of high percentages of excipients in the formulation, that it makes smaller quantities of active ingredient available in the preparation. That is why such preparations solve the problem of aerodynamic performance, but leave significant problems of chemical stability unsolved.

In terms of chemical stability, it could be more advantageous to prepare an inhalable powder by means of spray drying in which there is a high percentage content of active ingredient. For the best-known active ingredients used in respiratory therapies, this % content of active ingredient would in most cases be too high to enable the preparation of a drug in the form of an inhalable powder, given the minimal quantity of powder comprising a single dose of the product. Such a quantity of powder would be too small to be reproducibly metered by any industrial device for the production of single-dose inhalable powders. The preparation of an inhalable powder that is stable from both the chemical and the physical standpoints must therefore necessarily guarantee the following:

the stability of the active ingredients used;
an adequate aerosol performance, i.e. the deposition of a sufficient amount of the active ingredients in the lung.

For the purposes of chemical stability, an ideal approach involves preparing dry powders containing large quantities of active ingredient combined with a sugar capable of reducing their molecular mobility inside the particles of powder, and a hydrophobic excipient capable of limiting the powder's interaction with the outside environment and water absorption.

From the point of view of aerosol performance, the powder must be characterised by a particle size appropriate for its administration by inhalation and a composition capable of facilitating particle disaggregation when the powder is inhaled. At the same time, the combination of physical characteristics of the powder's composition has to coincide with the feasibility of its even distribution by both single-dose inhaler devices (for products in the form of inhalable powders in single doses), and multi-dose inhalers capable of repeatedly drawing off a dose that is not too small from a tank contained in the device.

The use of inhalable preparations has been amply described in the literature for the treatment of numerous diseases affecting the respiratory system. In particular, asthma and chronic obstructive pulmonary disease (COPD) tend to be preferentially treated by means of the administration of inhalable drugs.

Asthma is a chronic inflammatory disease of the airways. It is mainly characterised by an episodic airway obstruction and consequent expiratory flow limitation. The airway inflammation can sometimes be associated with structural changes. The prevalence of asthma is high and is gradually rising. It has been estimated that it ranges worldwide from 1% to 18% of the population, with an estimated 300 million people affected. Around the world, the deaths due to asthma have been estimated at 250,000 a year, and the mortality rate does not seem to correlate proportionally with the disease's prevalence. Although the cost of controlling asthma seems to be high for the patient, and for society at large, the costs associated with its non-treatment are even higher. The goal of treatment is to keep the asthma symptoms under control in order to optimise lung function and reduce symptoms, exacerbations, and the need for acute medical care and hospitalisation to a minimum. When the symptoms of asthma are controlled, recurrences and severe reacutizations are only rarely reported.

Chronic obstructive pulmonary disease (COPD) is characterised by chronic and persistent airflow limitation and a vast array of pathological changes in the lung, together with significant extra-pulmonary effects in individual patients that can contribute to the severity of their disease. The airflow limitation in COPD is not fully reversible and is associated with an anomalous inflammatory reaction in the lung to inhaled pollutants, such as harmful airborne particles or gases. COPD is generally a progressive disease, especially when a patient's exposure to the noxious agents is prolonged.

COPD is one of the main causes of morbidity and mortality around the world and gives rise to an important, ever-increasing economic and social burden. The prevalence of COPD is much higher in smokers and ex-smokers than in non-smokers, and in people over forty than in those under 40 years old, be they men or women. The estimated prevalence of COPD in the USA is 15 million patients over 40 years old. In European countries, the disease's estimated prevalence varies from 1.5 million people with COPD in Spain, to 3 million in the United Kingdom, 2.7 million in Germany, 2.6 million in Italy, and 2.6 million in France.

Estimates on COPD, which was classified in sixth position among the causes of death in 1990, indicate that it will become the third cause of death worldwide by the year 2020. This rising mortality rate is related to the epidemic expansion of smoking, to atmospheric pollutants, and to changing demographics in most countries, as their population's life expectancy increases.

The main pharmacological approach to asthma and COPD is based on the use of corticosteroids, administered by inhalation (ICS) or systemically (CS), either as a monotherapy or in association with bronchodilators (long-acting beta-agonists; LABA), long-acting anti-muscarinic drugs (LAMA), xanthine and other drugs.

Using LABA alone in asthma patients has been shown to increase the risk of asthma-related adverse events, including death, so their use is not recommended as a monotherapy. The risk of adverse events is lower with combinations of inhaled corticosteroids (ICS) and LABA. The use of ICS in combination with LABA will thus continue to be the standard treatment for diseases of the airways.

Molecular interactions between glucocorticoids and β2-adrenoreceptors may lie behind the clinical advantages achieved with the combination therapy. The glucocorticoids can increase the number of β2-adrenoreceptors, while the β2-agonists may induce a nuclear translocation and activation of the glucocorticoid receptors (GR).

For cases of persistent asthma, the international guidelines recommend using inhaled corticosteroids (ICS) at the lowest dose needed for symptom control, possibly in associated with a long-acting β2-agonist when the asthma symptoms cannot be controlled by the ICS alone. Associating LABA therapy with ICS increases the efficacy of the two drugs' combined effects in moderate and severe asthma.

In symptomatic adults on monotherapy with low or even high doses of ICS, it is common knowledge that associating a LABA with the ICS reduces the frequency of exacerbations demanding the administration of oral steroids, containing the symptoms and improving lung function. It also reduces the need to use short-acting β2-agonists as an emergency therapy.

In the case of COPD, current international guidelines indicate that none of the existing drugs have demonstrated the ability to modify the long-term deterioration in lung function that is the hallmark of this disease. Pharmacological therapy for COPD is consequently used to contain the symptoms or complications. Bronchodilators are fundamental to symptom management in COPD, used on demand or at regular intervals to prevent or reduce symptoms and reacutizations. Adding regular ICS treatment to the use of bronchodilators is appropriate for patients with symptomatic COPD who have a predicted FEV1<50% (stage III, severe COPD; and stage IV, very severe COPD) and recurrent exacerbations.

Although the combined use of ICS/LABA in dry powder inhaler (DPI) or pressurised metered-dose inhaler (pMDI) formulations is well-established in clinical practice, and the side-effects of ICS are less common and less severe than those of orally-administered steroids, a few considerations on the related safety issues are warranted, especially because any further research in this field should seek to overcome or at least contain them.

The main safety issues relating to the use of inhaled corticosteroids are explained below.

The overall therapeutic effect of ICS relies on their deposition in the airways, but most of the delivered dose (which depends on the inhaler used and the inhalation technique) is deposited in the upper airways (mouth, larynx and pharynx) and enters the gastrointestinal tract. Both absorption pathways (the gastrointestinal and the pulmonary) contribute to the drug's systemic bioavailability, which is potentially responsible for systemic side-effects. The dose deposited in the lower airways is absorbed directly into the systemic circulation and the part absorbed by the gastrointestinal tract is metabolised on its first passage through the liver.

Effects on the Oropharynx and Oesophagus

A significant fraction (up to 90%) of the delivered dose may be deposited in the mouth and pharynx. This carries the risk of local adverse effects, including oral and oesophageal candidosis, dysphonia, and cough. To limit the local adverse effects of ICS, it would be useful to reduce the quantity of ICS deposited on the oropharynx.

Suppression of the Hypothalamic-Pituitary-Adrenal (HPA) Axis

Long-term systemic exposure to exogenous glucocorticoids suppresses endogenous glucocorticoid production, so suddenly withdrawing the exogenous agent can cause acute to adrenal insufficiency and adrenal crisis.

Effect on the Skin and Ecchymoses

The use of ICS is associated with a reduced collagen synthesis in the skin. High-dose ICS therapy leads to skin thinning and ecchymoses, and also to slow skin healing in response to cuts and other lesions.

Effects on Growth and Bone Mineral Density

Although the effects of ICS are controversial, it is well known that corticosteroids tend to influence bone mineral density, particularly in the spine.

Other very important problems relating to the use of ICS concern the potential pharmacological interactions with other active ingredients. All currently-available ICS undergo extensive metabolic conversion in the liver due primarily to the effect of enzymes in the CYP3A4 family. That is why, in clinical practice, lower doses of ICS should be used, co-administered with CYP3A4 inhibitors.

The role of ICS in cataracts and glaucoma, and their potential effects on insulin resistance are still being debated. Even if the side-effects of ICS are less frequent and less severe than those of oral steroids, concerns remain about their safety.

In addition, approximately 5-10% of all asthma patients fail to respond adequately even to oral steroids. As for COPD, treatment with ICS raises the probability of pneumonia and does not reduce the overall mortality rate. The dose-response relationship and long-term safety of ICS in COPD are still not known. Only moderate or high doses have been used in long-term clinical studies.

The US Food and Drug Administration (FDA) has recently issued recommendations for restricting the use of LABA in the treatment of asthma. The development of new formulations to limit the systemic burden of both ICS and LABA thus appears to be justified and focused on covering therapeutic needs.

As mentioned previously, the main pharmacological approach to care and treatment for asthma and COPD is currently based on the use of inhaled corticosteroids (ICS) associated with long-acting beta-agonist (LABA) bronchodilators. In particular, the reference pharmacological solution currently available on the market associates budesonide with formoterol fumarate, formulated in three different dosages.

Budesonide is an anti-inflammatory corticosteroid that exhibits a powerful glucocorticoid activity and a weak mineralocorticoid activity. Its absorption in the tissues of the airways does not seem to be influenced by lung function, comparable plasma concentrations being achieved after its administration in the lungs of healthy and asthmatic individuals. After absorption at intracellular level, budesonide undergoes a reversible conjugation with intracellular fatty acids that prolong its preservation within the airways and its action.

Formoterol fumarate is a long-acting selective beta-2-adrenergic receptor agonist (LABA) with a rapid onset of action. Its solubility in water and moderate lipophilia guarantee a rapid diffusion towards the β2-adrenoreceptors on the smooth muscle cells of the airways with a rapid bronchodilating effect.

The patent EP0613371 describes a solid formulation for inhalation comprising budesonide and formoterol. The formulation is obtained by micronisation of the active ingredients, which are subsequently suspended or dissolved in a suitable propellant liquid. This solution has some technological limitations, however, due both to the nature of the active ingredients in micronised solid form, and to the mode of administration using pressurised inhalers. In fact, when the active ingredients are micronised and dispersed in a propellant in a solid state, they are unable to reach the lowermost parts of the lung effectively. While in storage, the products tend to become compacted and form clumps of particles of a size unsuitable for administration in the lung. That is why the two active ingredients are contained in larger quantities in this type of formulation, in order to compensate for the paucity of drug being deposited at the site of action (due to the clumps of particles being of inappropriate size). This means that the amounts of active ingredient deposited outside the lung increase, with a consequent potential increase in the side-effects typical of corticosteroids and β2-agonists. In these formulations, moreover, the doses of powder and active ingredient delivered by the inhaler are sometimes scarcely reproducible because the clumps of particles that develop interfere with the delivery of the powder during the drug's administration.

In the light of all the above considerations, it would be advantageous to be able to prepare an inhalable pharmaceutical composition for the treatment of asthma and chronic obstructive pulmonary disease (COPD) in the form of a dry powder that remains stable and easy to administer with normal powder inhaler devices, and that are easy to manufacture at the same time.

According to the current state of the art, the problem of providing an inhalable formula containing drugs for treating asthma and COPD that enables a satisfactory pharmacological response to be obtained while markedly reducing the quantities of ICS and LABA contained in the formulations thus remains wholly or partially unsolved. Solving this problem could potentially reduce the previously-described issues. It would also be useful to have an inhalable powder for the treatment of asthma and COPD that:
  enables reproducible doses of both the ICS and the LABA to be obtained when the formulation is administered using common powder inhalers;
  is easy for all patients to inhale, including those with inspiratory difficulties due to respiratory muscle weakness; such patients would be unable to use a high-resistance powder dispenser and the efficacy of the drug would consequently be impaired.

A first aspect of the present invention thus relates to the preparation of a pharmaceutical composition for inhalation comprising:

a) a first powder comprising budesonide or a pharmaceutically acceptable salt thereof, in amounts greater than 5% by weight of said first powder, leucine in amount from 5 to 70% by weight of said first powder, lactose in amount from 20 to 90% by weight of said first powder;
b) a second powder comprising formoterol or a pharmaceutically acceptable salt thereof, in an amount greater than 1% by weight of said second powder, leucine in amount from 5 to 70% by weight of said second powder, lactose in amount from 20 to 90% by weight of said second powder;
c) a third powder comprising leucine in amount from 5 to 70% by weight of said third powder and lactose in amount from 20 to 90% by weight of said third powder;

wherein said composition has a fine particle fraction (FPF) greater than 60% and a delivered fraction (DF) greater than 80%.

Another aspect of the invention concerns a kit for administering a drug in the form of an inhalable powder comprising a metered quantity of the composition according to the present invention and an inhaler device.

In particular, the budesonide in the first powder in the composition according to the present invention comprises a quantity greater than 7% w/w of the powder in which it is contained. The formoterol in the second powder in the composition according to the present invention comprises a quantity greater than 2% w/w of the powder in which it is contained.

As for the molar ratio between the two active ingredients in the composition forming the object of the present invention, the molar ratio between the budesonide and formoterol is from 15:1 to 40:1, preferably in the range of 5:1 to 120:1, more preferably between 8:1 and 71:1, and better still between 17:1 and 36:1.

Analysing the composition in quantitative terms, the budesonide contained in the above-described formulation is in quantities in the range of 30 to 180 µg, while the formoterol content is in quantities in the range of 1.5 to 5.5 µg per inhaled unit dose. The term 'inhaled unit dose' is used to mean the dose delivered from the mouthpiece of the inhaler with each single inhalation.

In a first preferred embodiment of the inhalable composition, the budesonide content is in quantities in the range of 35 to 45 µg, and the formoterol content is in quantities in the range of 1.5 to 3 µg per inhaled unit dose.

In a second preferred embodiment, the budesonide content is in quantities in the range of 75 to 85 µg, and the formoterol content is in quantities in the range of 1.5 to 3 µg per inhaled unit dose.

In a third preferred embodiment, the budesonide content is in quantities in the range of 155 to 165 µg, and the formoterol content is in quantities in the range of 4 to 5 µg per inhaled unit dose.

According to the present invention, the powders contained in the pharmaceutical preparation forming the object of the present description include a hydrophobic substance to reduce their sensitivity to humidity. This hydrophobic substance is leucine, which also facilitates the disaggregation of the particles. The leucine content is in the range of 5 to 70% w/w of each powder. The quantity of leucine included in the powders contained in the pharmaceutical composition is preferably in the range of 18 to 55% w/w of each powder.

The powders contained in the pharmaceutical composition forming the object of the present description also include lactose, a disaccharide sugar, in quantities in the range of 20 to 90%, and preferably in quantities in the range of 40 to 80% w/w of each powder.

According to the present invention, the first, second and third powders contained in the composition include a surfactant in quantities in the range of 0.2 to 2% w/w of each powder, and preferably in quantities in the range of 0.4 to 0.8% w/w of each powder.

The surfactant in the composition according to the invention can be chosen from among various classes of surfactants for pharmaceutical use. The surfactants suitable for use in the present invention can be all those substances characterised by a medium or low molecular weight and that contain a hydrophobic portion, which is generally readily soluble in an organic solvent but weakly soluble or entirely insoluble in water, and a hydrophilic (or polar) portion that is weakly soluble or entirely insoluble in an organic solvent but readily soluble in water. Surfactants are classified according to their polar portion, so surfactants with a negatively-charged polar portion are defined as anionic surfactants, while cationic surfactants have a positively-charged polar portion. Surfactants that are not charged are generally defined as non-ionic, while surfactants that contain both positively- and negatively-charged groups are called zwitterionic. Examples of anionic surfactants include fatty acid salts (better known as soaps), sulphates, ether sulphates and phosphate esters. Cationic surfactants are frequently based on polar groups containing amine groups. The most common non-ionic surfactants are based on polar groups containing oligo-(ethylene oxide) groups. The zwitterionic surfactants are generally characterised by a polar group comprising a quaternary amine and a sulphuric or carboxylic group.

The following surfactants are specific examples of this application: benzalkonium chloride, cetrimide, sodium docusate, glyceryl monooleate, sorbitan esters, sodium lauryl sulphate, polysorbates, phospholipids, bile salts. Non-ionic surfactants are preferable, such as polysorbates and polyoxyethylene and polyoxypropylene block copolymers, known as "poloxamers". Polysorbates are described in the CTFA International Cosmetic Ingredient Dictionary as mixtures of sorbitol fatty acid esters and condensed sorbitol anhydrides with ethylene oxide. Particular preference goes to the non-ionic surfactants in the series known as "Tween", and particularly the surfactant known as "Tween 80", a commercially-available polyoxyethylene sorbitan monooleate.

The inclusion of a surfactant, and preferably of Tween 80, is necessary to eliminate electrostatic charges detected in formulations without it, and to ensure the powder's flowability and the maintenance of a homogeneous solid state, with no initial crystallisation. According to the present invention, the term "inhalable" is used to mean that the powder is appropriate for administration in the lung. An inhalable powder can be dispersed and inhaled by means of a suitable inhaler, so that the particles can enter the lung and reach the alveoli where the pharmacological characteristics of the active ingredients it contains can take effect. A particle with an aerodynamic diameter of less than 5.0 μm is generally considered inhalable.

The term "amorphous" is used according to the present invention to mean that the powder contains less than 70% of crystalline fraction, and preferably less than 55%. The pharmaceutical composition described herein has a w/w ratio of the powder in amorphous form contained in the composition to the sugar contained in the composition that ranges from 0.8 to 2.0. This ratio indicates that the sugar contained in the powder is a substantially amorphous sugar, and consequently has a crystalline fraction of less than 50%. This enables the sugar to coordinate the water contained in the composition, preventing it from becoming available to hydrolyse the active ingredient and consequently make it ineffective.

The pharmaceutical composition as described in the second embodiment can be used to obtain a pharmacologically active preparation comprising a combination of two or more different active ingredients that may have a synergic action or simply take effect simultaneously at the site of application in order to reduce the number of administrations.

The term "fine particle fraction" (FPF)" is used to mean the amount of powder, in relation to the total amount of powder delivered by an inhaler, that has an aerodynamic diameter (dae) below 5.0 μm. Characterisation tests conducted to assess this property in the powder are done with the Multi-Stage Liquid Impinger (MSLI), as described in the current edition of the European Pharmacopoeia. The conditions for performing this test consist in aspirating the powder through the inhaler so as to generate a flow of 60 L per minute. This flow is produced by generating a 2 kPa pressure drop in the system.

The term "delivered fraction" (DF) is used to mean the proportion of the total amount of active ingredient that is delivered by a powder inhaler under standard conditions of aspiration. The characterisation test conducted to assess this property of the powder is the DUSA, as described in the current edition of the European Pharmacopoeia. The conditions for performing this test consist in aspirating the powder through an inhaler so as to generate a 4 kPa pressure drop in the system.

The preferred production process for the powder according to the invention is spray drying, starting from a solution of leucine, a sugar and a surfactant in which the drug (if any) is dissolved or dispersed as a suspension or emulsion.

As for the preferred particle size of said powder, at least 50% of the particle size distribution (X50) should be below 5 μm, and preferably below 3 μm, and better still below 2.0 μm, here again to increase the surface area covered and thereby optimise the drug's deposition in the lower lung.

According to the present invention, the powder comprising the pharmaceutical preparation is a substantially dry powder, i.e. a powder that has a humidity content of less than 10%, and preferably less than 5%, or better still less than 3%. This dry powder preferably contains no water capable of hydrolysing and inactivating the active ingredient. The amount of humidity contained in the preparation is controlled by:

- the presence of leucine, because its characteristic hydrophobicity limits the water content both during the production of the powder and during its subsequent manipulation;
- the presence of sugar that, by trapping the humidity in a structure that becomes increasingly rigid with time, preventing the water from becoming available to hydrolyse the active ingredient.

The process for preparing the pharmaceutical composition according to the invention essentially comprises the following steps:

a) obtaining by spray drying at least a first powder comprising an active ingredient in a quantity greater than 1% w/w of the powder, leucine in a quantity comprised between 5 and 70% w/w of the powder, and lactose that is substantially amorphous after the powder has been obtained by spray drying in a quantity comprised between 20 and 90% w/w of the powder;

b) obtaining by spray drying a second powder comprising leucine in a quantity comprised between 5 and 70% w/w of the powder, and lactose that is substantially amorphous after the powder has been obtained by spray drying in a quantity comprised between 20 and 90% w/w of the powder; and c) blending the two powders.

In particular, in steps (a) and (b), the composition production process to obtain the powders by spray drying consists in a series of steps as outlined below.

For step (a), these steps include:
preparing a first phase (A), in which an active ingredient is contained in an appropriate liquid medium;
preparing a second phase (B), in which leucine, lactose and surfactants are dissolved or dispersed in an aqueous medium;
mixing said phases (A) and (B) to obtain a third phase (C), in which the liquid medium is homogeneous;
drying said phase (C) under controlled conditions to obtain a dry powder with a particle size distribution wherein the median diameter is less than 10.0 μm;
collecting said dry powder.

Phase (A) may be a suspension of the active ingredient in an aqueous or non-aqueous medium, or a solution of the active ingredient in an appropriate solvent. The preparation of a solution is preferred, and the organic solvent is chosen from among those suitable for mixing with water. In this case, phase (C) is also a solution of all of the ingredients in the composition.

When, on the other hand, phase (A) is a suspension of the hydrophobic active ingredient in an aqueous medium, then phase (C) is also a suspension in an aqueous medium, which will contain the soluble components dissolved therein, including the excipients and surfactants.

The drying process consists in eliminating the liquid medium—solvent or dispersant—from phase (C) to obtain a dry powder with the required particle size characteristics. This is probably done by means of a spray drying process. The characteristics of the nozzle and the process parameters are chosen so that the liquid medium evaporates from the solution or suspension (C) and a powder of the required particle size is obtained.

For phase (B), the steps include:
preparing a first phase (A), in which leucine, lactose and surfactants are dissolved or dispersed in an aqueous medium;
drying said phase (A) under controlled conditions to obtain a dry powder with a particle size distribution such that the median diameter is less than 10.0 μm;
collecting said dry powder.

Phase (C) of the process for preparing the pharmaceutical composition consists in physically blending the powders obtained by spray drying using any common blending technique, such as the revolving-body Turbula shaker-mixer, V-mixer, or cylindrical, biconical, or cube-shaped fixed-body mixers, used for blending alone (such as the planetary, nautamix, sigma and ribbon blenders), or for granulating too (such as the Diosna). In addition to these mixers, it would also be possible to blend the powders with devices normally used to mix liquids, such as the Ultraturrax or Silverson, or even in fluid bed granulating appliances.

According to the present invention, the inhalable pharmaceutical formulation comprises budesonide and formoterol, and is mainly used for the treatment of asthma (for maintenance therapy and on demand), and chronic obstructive pulmonary disease (COPD).

Given the aerodynamic performance of the inhalable pharmaceutical composition according to the present invention, thanks mainly to the morphology of the powders and the process used for their preparation, which enables the deposition of a large proportion of the powder at the intended site of action (in the lung), an effective therapeutic action on the disease being treated can be achieved with the administration of a smaller quantity of active ingredient. In particular, with an inhalable pharmaceutical composition according to the present description, the doses of active ingredient that need to be administered can be halved by comparison with the doses of active ingredient currently administered for the treatment of certain diseases. Reducing the content of active ingredient consequently reduces the side-effects typical of drugs containing corticosteroids and β2-agonists.

EXAMPLES

Methods for preparing the powders contained in the pharmaceutical composition forming the object of the present invention are described below.

Preparation of the Single Powders

The powders containing the active ingredients and the powder used to dilute them (hereinafter called 'bulking agent') were obtained by spray drying, a drying method that enables amorphous powders to be obtained with a uniform particle size distribution from solutions of active ingredients and excipients prepared in a suitable solvent or mixture of solvents.

For the formulations described herein, the solvents used were water and ethyl alcohol in a fixed ratio of 70/30. The concentration of dissolved solids was 1% weight to volume (w/v) for the formulations containing the active ingredient, and 2% w/v for the bulking agent.

In the case of the powder containing formoterol fumarate as the active ingredient and a bulking agent, all the components of the powder were dissolved in water and the resulting solution was slowly added to the portion of ethyl alcohol at 25° C.

In the formulation containing budesonide as the active ingredient, this active ingredient was dissolved separately in the alcoholic portion, to which the aqueous solution containing the excipients was then added to obtain a single hydro-alcoholic solution. The resulting hydro-alcoholic solution was processed with a Buchi Mod. B290 spray drier using an open cycle with the following parameters:

nozzle diameter: 0.7 mm
atomising gas: nitrogen
atomising pressure: 4 bar
drying gas: air
100% aspiration (35 m$^3$/h)
inlet temperature 170° C.
delivery rate 8% (2.4 ml/min)
powder collection system: cyclonic separator with glass container for powder collection (External diameter: 8.5 cm. Height: 30.5 cm)
outlet filter: nylon sleeve, At the end of the drying process, the powder collection phase was completed in controlled temperature and humidity conditions: temperature <25° C., relative humidity <35%.

The powders were packaged immediately after production in borosilicate glass ampoules and placed in a double aluminium envelope sealed by heat-welding under a partial vacuum (30%).

Preparation of the Mixtures

The formulations described in the examples were obtained by blending the powders containing the active ingredients plus a powder containing the bulking agent.

Irrespective of the quantitative ratios between the initial powders, a layered blending technique was used, arranging the powder containing the active ingredient between two layers of bulking agent inside the mixer's container. An Ultra Turrax T10 mixer was used to blend the powders, mixing them for 5 minutes, a time considered sufficient for the 3.5 g of powder contained in each of the batches produced. Content uniformity was checked by means of titre analysis on 10 samples collected from different points in the bulk.

The powders were transferred to bottles, sealed and stored in a double aluminium envelope sealed by heat-welding under a partial vacuum (30%).

The blending and distribution of the powder in the bottles were done inside a glove box in controlled humidity and temperature conditions: maximum temperature 20° C. and relative ambient humidity <35%.

Storage Conditions for Accelerated Stability Studies

During the accelerated stability study, the powders, packaged as described above, were stored in an oven at a temperature of 40° C. and a relative humidity of 13%.

At each time point established for the study, the samples corresponding to the stability point were collected, left to cool until they reached room temperature, then opened under controlled conditions in a glove box (temperature <20° C., RH<35%), and analysed as established in the protocol.

Powder Characterisation: Dimensional Analysis

The powders obtained were characterised in terms of their particle size distribution in dry conditions using a Sympatec Helos light scattering appliance (which analyses the size of the particles according to the Fraunhofer theory), equipped with a RODOS disperser. The instrument was appropriately calibrated with the reference material and prepared according to the instructions in the instrument's instruction manual.

After adequate cleaning prior to the analysis, an aliquot of powder from each production batch was analysed with no preliminary preparation of the sample concerned. The dispersion gas used was compressed air, suitably filtered to remove any particle matter. The established analytical method thus involved taking the following precautions relating to the sample, the powder disperser and the light scattering analyser.

Sample
  size: 100 mg approx.
  delivery procedure: with a spatula
  sample pre-treatment: none
RODOS disperser
  model M ID-NR 230 V/Hz 24Va
  dispersion pressure: 3 bar
Light Scattering Analyser
  model: Helos
  analytical method: Fraunhofer
  software version: Windox 4.0
  lens: R1 (0.1-35 μm)
  minimum optical concentration: 1%
  analytical activation threshold: a minimum optical concentration detectable of 1% for a maximum of 30 seconds with at least 100 ms of exposure of the sample.

All the analyses were conducted under controlled temperature and humidity conditions: temperature <25° C. and relative humidity <50% RH. The dimensional analysis returned values indicating a volume mean diameter (VMD) of the population of particles in the sample of powder.

Powder Characterisation: Residual Humidity Content

The residual humidity content in the powder was measured using the Karl Fischer method, coulometric system. This was done with the C20 Compact Karl Fischer Coulometer (Mettler Toledo), which uses HYDRANAL®-Coulomat AG as a reagent.

The powder samples were accurately weighed in quantities of approximately 15-20 mg, recording their weight among the sample parameters. Titration began immediately after placing the sample in the reagent solvent bath. After the analysis, the instrument directly reports the percentage of water contained in the sample.

Powder Characterisation: Titration and Correlates

HPLC (high-performance liquid chromatography) was used to ascertain the content of active ingredients and their correlated substances. The analytical method was characterised by the following parameters:

Solvent: 50/50 methanol/phosphate buffer pH 2.7 25 mM
Mobile phase: acetonitrile/phosphate buffer pH 2.9 2.82 Mm
Gradient elution:

| Time (min) | % ACN | % buffer pH 2.9 | Flow rate (ml/min) |
|---|---|---|---|
| 0 | 22 | 78 | 0.5 |
| 2.5 | 22 | 78 | 0.5 |
| 3.0 | 41 | 59 | 0.7 |
| 8.0 | 41 | 59 | 0.7 |
| 10.0 | 70 | 30 | 0.7 |
| 12.0 | 22 | 78 | 0.6 |
| 15.0 | 22 | 78 | 0.6 |

Injection volume: 20 μL
Analytical column: Agilent Poroshell 120 EC-C18, 100 mm×3.0 mm, 2.7 μm
Column temperature: 30° C.
Wavelengths: 220 nm (formoterol fumarate) and 240 nm (budesonide)
Retention times: 2.4 min (formoterol fumarate) and 8.0 min (budesonide)

The HPLC Agilent model 1200 was used for the analyses, with a model G1315C diode array detector. The samples used in the analyses were obtained by dissolving in the solvent a quantity of powder sufficient to obtain a concentration of 160 μg/ml for the budesonide, and 4.5 μg/ml for the formoterol fumarate, as for the reference solution. The reference solution was injected three times consecutively before the sample to check the system's precision, expressed as the percentage of relative standard deviation (RSD %), which must be less than 2%.

The content of the active ingredients was measured by correlating the areas with a reference solution of known concentration. Product degradation was calculated as the ratio between the sum of the areas of all the analytical peaks corresponding to the degradation products and the reference active ingredient. The sum of the degradation products included all the analytical peaks with an area on the chromatogram greater than 0.1% of the area of the active ingredient.

Powder Characterisation: Differential Scanning Calorimetry

Differential scanning calorimetry (DSC) is a thermoanalytical technique used to identify chemical-physical phenomena with endo- or exothermal effects in a sample, such as phase changes, water loss, or chemical reactions. For DSC, the sample is heated at a constant rate and the quantity of heat needed to raise its temperature depends on its thermal capacity. Each endo- and exothermal phenomenon reversibly or irreversibly modifies the thermal capacity of the material and can be identified as a variation in the baseline on the thermogram.

During heating, formulations containing amorphous lactose show a typical drop in their thermal capacity corresponding to a glass-rubber transition of the lactose from the amorphous solid state to a metastable state that rapidly leads to crystallisation, characterised by an exothermal peak. The temperature corresponding to these phenomena varies, depending on the composition of the sample and the ambient conditions of its storage and preparation.

The samples were prepared under controlled ambient conditions (temperature <20° C., relative humidity 35-30%). Standard aluminium 40 μL DSC crucibles were filled with a weighed quantity of 1 to 3 mg of powder and sealed with a specific cover. The colorimetric analysis on the samples being tested was then conducted, submitting the samples to a heating ramp from 20 to 200° C., increasing the temperature in steps of 10° C./min. The analysis returns a thermogram showing the thermal events that accompany the gradual heating of the sample. Glass-rubber transition (Tg) is identifiable from a descending step, sometimes followed by an upward step, in the baseline caused by enthalpy relaxation. When the thermograms are analysed, the temperature at which the phenomenon begins (Tg onset) is calculated irrespective of the size of the sample. The glass-rubber transition temperature gives an indication of the powder's stability because Tg occurs before crystallisation, which takes place above 100° C. The exothermal peak on crystallisation can be integrated and the area under the curve provides an indication of the amorphous fraction of the sample.

Powder Characterisation: Inhalability Test with the MSLI

The Multi-Stage Liquid Impinger (MSLI) is an appliance for simulating the deposition in the lung of an inhaled formulation in vitro. An inhalable formulation delivered by an appropriate inhaler or conveyed inside the appliance by aspiration, is sequentially deposited in the various stages of the impinger, depending on the powder's aerodynamic characteristics such as particle size, density and shape. Each stage of the MSLI corresponds to a range of the aerodynamic particle sizes of the powder deposited inside it. HPLC analysis of the quantity of active ingredient in each stage are used to identify the aerodynamic size distribution of the powder, and it is possible to calculate the mass median aerodynamic diameter (MMAD), as well as the inhalable fraction (also known as fine particle fraction, FPF), which is the fraction with an aerodynamic diameter <5.0 μm according to the European Pharmacopoeia. For the inhalability test, the powders in the formulations used in the examples were placed in No. 3 HPMC capsules and charged with the RS01 powder inhaler—model 7 for single doses, code 239700001AB (Aerolizer—Plastiape S.p.A.). The appliance was assembled according to the manufacturer's instructions and the recommendations of the European Pharmacopoeia. For analytical reasons it was necessary to deliver 10 capsules of powder for each inhalability test. The tests were conducted at a flow rate of 60 L/min for 4 seconds, with a 2 kPa pressure drop in the system. At this flow rate, each stage corresponded to the following aerodynamic diameter cut-offs:

stage 1: >13 μm
stage 2: from 13 μm to 6.8 μm
stage 3: from 6.8 μm to 3.1 μm
stage 4: from 3.1 μm to 1.7 μm
stage 5 (filter): <1.7 μm The inhalable fraction (or Fine Particle Fraction) includes particles with an aerodynamic diameter of less than 5.0 μm and was calculated using a specific software (CITDAS Copley). The aerodynamic parameters of an inhalable formulation analysed with the MSLI are expressed in terms of:

Delivered Fraction (DF): i.e. the percentage of the dose of active ingredient that emerges from the inhaler's mouthpiece;

Fine Particle Dose (FPD): the inhalable dose of active ingredient with a diameter <5.0 μm;

Fine Particle Fraction (FPF): the inhalable fraction (aerodynamic diameter <5.0 μm) of the active ingredient expressed as a proportion of the quantity delivered;

Mass Median Aerodynamic Diameter (MMAD): the median aerodynamic diameter of the particles delivered.

The active ingredient in each stage was quantified by HPLC using the analytical method by content and degradation products.

Example 1

Example 1 was conducted preparing powder containing formoterol fumarate, which is an active ingredient sensitive to the presence of free water in the formulation. Powder containing different quantities of leucine, and lactose or mannitol were prepared together with the formoterol. The example demonstrated the protective effect of lactose on the formoterol; this protective effect is explained by the fact that lactose is capable of having a "scavenger" effect on the free water contained in the formulation. Three types of powder were produced to demonstrate this:

powder containing only formoterol and leucine;

2 powders containing different amounts of lactose together with formoterol and leucine;

2 powders in which the lactose was replaced with a different sugar, i.e. mannitol.

powder containing lactose tend to absorb humidity over time, with a consequent reduction of the Tg, but the degradation over time is limited. This limited degradation is presumably due to a scavenger effect of the lactose on water, which is consequently trapped within a rigid structure that prevents it from reacting with the other ingredients. The powder containing no lactose, on the other hand, was already crystalline at the start and underwent chemical degradation.

Between the two powders containing lactose, the one with 50% proved better because it was more stable over time.

TABLE 1A

| Ex. | Active ingredient | Formoterol (%) | Leucine % | Sugar | Water content (%) T0 | Water content (%) T28 (days) |
|---|---|---|---|---|---|---|
| 1 | formoterol | 5 | 95 | No sugar | 0.9 | 0.9 |
| 2 | formoterol | 5 | 70 | Lactose | 1.4 | 1.8 |
| 3 | formoterol | 5 | 45 | Lactose | 2.1 | 2.7 |
| 4 | formoterol | 5 | 70 | Mannitol | 0.9 | 0.9 |
| 5 | formoterol | 5 | 45 | Mannitol | 1 | 0.9 |

TABLE 1B

| Ex. | Tg (° C.) T0 | Tg (° C.) T28 days | P. size (μm) T0 | P. size (μm) T28 days | Degradation (%) T0 | Degradation (%) T28 days |
|---|---|---|---|---|---|---|
| 1 | Not recorded | Not recorded | 2.6 | 2.7 | 0.6 | 0.9 |
| 2 | 62.7 | 56.9 | 2 | 1.9 | 0.4 | 0.4 |
| 3 | 66.3 | 57.5 | 1.6 | 1.6 | 0.3 | 0.3 |
| 4 | Not recorded | Not recorded | 2.3 | 2.2 | 0.2 | 1.6 |
| 5 | Not recorded | Not recorded | 1.6 | 1.6 | 0.1 | 1.4 |

According to the present invention, the powder is acceptable, i.e. it satisfies the optimal parameters for administration by inhalation, when:

- the products of degradation are less than 1% of the total active ingredient at the time T0 (product of degradation T0<1% tot);
- the delivered fraction, i.e. the percentage of the dose of active ingredient delivered through the mouthpiece of the inhaler, is higher than 80% at the time T3 (DF T3>80%);
- the fine particle fraction, i.e. the quantity of fine particles of active ingredient less than 5 μm in size, is more than 60% at the time T0, and at the time T3 (FPF T0 and T3>60%).

TABLE 2A

| Ex. | Active ingredient | HLSA Bud (composition %) Bud | HLSA Bud (composition %) Leucine | HLSA Bud (composition %) Lactose | HLSA Bud (composition %) Tween 80 | BA (composition %) Leucine | BA (composition %) Lactose | BA (composition %) Tween 80 | Blend of powders HLSA Bud (mg) | Blend of powders BA (mg) |
|---|---|---|---|---|---|---|---|---|---|---|
| 6 | budesonide | 8 | 0 | 91.5 | 0.5 | | | | 5 | 0 |
| 7 | budesonide | 8 | 50 | 41.5 | 0.5 | | | | 5 | 0 |
| 8 | budesonide | 8 | 91.5 | 0 | 0.5 | | | | 5 | 0 |
| 9 | budesonide | 8 | 0 | 91.5 | 0.5 | 0 | 99.5 | 0.5 | 0.1 | 9.9 |
| 11 | budesonide | 8 | 0 | 91.5 | 0.5 | 50 | 49.5 | 0.5 | 0.1 | 9.9 |
| 12 | budesonide | 8 | 0 | 91.5 | 0.5 | 99.5 | 0 | 0.5 | 0.1 | 9.9 |
| 13 | budesonide | 8 | 50 | 41.5 | 0.5 | 0 | 99.5 | 0.5 | 0.1 | 9.9 |
| 14 | budesonide | 8 | 50 | 41.5 | 0.5 | 50 | 49.5 | 0.5 | 0.1 | 9.9 |
| 15 | budesonide | 8 | 50 | 41.5 | 0.5 | 99.5 | 0 | 0.5 | 0.1 | 9.9 |
| 16 | budesonide | 8 | 91.5 | 0 | 0.5 | 0 | 99.5 | 0.5 | 0.1 | 9.9 |
| 17 | budesonide | 8 | 91.5 | 0 | 0.5 | 50 | 49.5 | 0.5 | 0.1 | 9.9 |
| 18 | budesonide | 8 | 91.5 | 0 | 0.5 | 99.5 | 0 | 0.5 | 0.1 | 9.9 |

Example 2

Example 2 was conducted preparing powders containing budesonide as active ingredient (named HLSA Bud in the table), with lactose and leucine in two different quantities. Other formulations containing lactose and leucine, with three different quantities of leucine and using lactose as a bulking agent (named BA in the table), i.e. powders containing leucine and lactose but no active ingredient, were prepared together with the formulations containing budesonide. The inclusion of leucine in three different quantities 0%, 50% and 91.5% was used to test its disaggregating properties in the formulation, with positive effects on parameters such as the Delivered Fraction and Fine Particle Fraction.

After preparing the powders for examples 12, 13 and 14, these powders were mixed with three types of bulking agent powder. These three bulking agents also contained leucine in three different quantities (0%, 50% and 99.5%). This further part of the study demonstrated that the bulking agent was able to facilitate the complete emptying of the capsule. The composition of the bulking agent is crucial, however, because a bulking agent excessively rich in leucine produces chemical degradation effects on the active ingredient.

TABLE 2B

| Ex. | Water content (%) T0 | Water content (%) T3 | Particle size (μm) T0 | Particle size (μm) T3 | % content of active ingredient T0 | % content of active ingredient T3 |
|---|---|---|---|---|---|---|
| 6 | 2.6 | 2.3 | 2.0 | 2.2 | 102.9 | 102.3 |
| 7 | 1.9 | 1.6 | 1.9 | 1.9 | 101.4 | 99.3 |
| 8 | 0.7 | 0.4 | 3.0 | 3.0 | 89.3 | 91.6 |
| 9 | 2.6 | 1.9 | 3.1 | 4.4 | 95.9 | 101.9 |
| 11 | 2.2 | 2.0 | 2.1 | 1.9 | 101.3 | 104.6 |
| 12 | 1.0 | 0.4 | 3.2 | 3.7 | 103.4 | 100.2 |
| 13 | 2.7 | 1.7 | 2.9 | 4.5 | 102.2 | 95.3 |
| 14 | 2.6 | 2.1 | 2.0 | 2.0 | 99.3 | 103.1 |
| 15 | 0.9 | 0.5 | 3.2 | 3.4 | 92.9 | 83.4 |
| 16 | 2.9 | 1.9 | 3.6 | 3.8 | 98.8 | 89 |
| 17 | 2.3 | 2.3 | 2.4 | 2.4 | 99.8 | 92.6 |
| 18 | 0.4 | 0.4 | 3.3 | 3.5 | 91.4 | 62.8 |

TABLE 2C

| Ex. | Degradation (%) T0 | Degradation (%) T3 | Degradation (%) Growth | DF (%) T0 | DF (%) T3 | FPF (%) T0 | FPF (%) T3 |
|---|---|---|---|---|---|---|---|
| 6 | 0.0 | 0.0 | 0.0 | 73.7 | 73.6 | 45.8 | 37.9 |
| 7 | 0.4 | 0.7 | 0.3 | 79.1 | 79.0 | 67.6 | 74.4 |
| 8 | 1.6 | 4.4 | 2.8 | 92.6 | 93.1 | 69.6 | 78.5 |
| 9 | 0.0 | 0.4 | 0.4 | 94.3 | 94.6 | 35.5 | 24.0 |
| 11 | 0.0 | 0.4 | 0.4 | 92.9 | 94.7 | 44.1 | 40.0 |
| 12 | 0.0 | 1.9 | 1.9 | 96 | 96.0 | 44.3 | 33.7 |
| 13 | 0.4 | 0.7 | 0.3 | 95.6 | 95.6 | 44.3 | 27.2 |
| 14 | 0.4 | 1.5 | 1.1 | 94.4 | 95.5 | 64.6 | 75.2 |
| 15 | 0.4 | 13.2 | 12.8 | 96 | 95.8 | 57.5 | 65.6 |
| 16 | 1.7 | 3.0 | 1.3 | 95.9 | 95.5 | 47.2 | 18.5 |

TABLE 2C-continued

| | Degradation (%) | | | DF (%) | | FPF (%) | |
|---|---|---|---|---|---|---|---|
| Ex. | T0 | T3 | Growth | T0 | T3 | T0 | T3 |
| 17 | 1.7 | 5.6 | 3.9 | 92.3 | 95.7 | 51.3 | 72.0 |
| 18 | 1.8 | 23.7 | 21.9 | 95.8 | 97.0 | 47.2 | 79.4 |

Example 3

This example was conducted preparing powder containing formoterol fumarate (named as HLSA FF in the table) as the active ingredient, with lactose and leucine in two different quantities. Other powder containing lactose and leucine, with three different quantities of leucine and using lactose as a bulking agent (named BA in the table), i.e. powders containing leucine and lactose but no active ingredient, were prepared together with the formulations containing formoterol fumarate. The inclusion of leucine in three different quantities 0%, 50% and 91.5% was used to test its disaggregating properties in the formulation, with positive effects on parameters such as the Delivered Fraction and Fine Particle Fraction.

After preparing the powders for examples 12, 13 and 14, these powders were mixed with three types of bulking agent powder. These three bulking agents also contained leucine in three different quantities (0%, 50% and 99.5%). This further part of the study demonstrated that the bulking agent was able to facilitate the complete emptying of the capsule. The composition of the bulking agent is crucial, however, because a bulking agent excessively rich in leucine produces chemical degradation effects on the active ingredient.

According to the present invention, the powder is acceptable, i.e. it satisfies the optimal parameters for administration by inhalation, when:
- the products of degradation are less than 1% of the total active ingredient at the time T0 (product of degradation T0<1% tot);
- the delivered fraction, i.e. the percentage of the dose of active ingredient delivered through the mouthpiece of the inhaler, is higher than 80% at the time T3 (DF T3>80%);
- the fine particle fraction, i.e. the quantity of fine particles of active ingredient less than 5 μm in size, is more than 60% at the time T0, and at the time T3 (FPF T0 and T3>60%).

TABLE 3A

| | | HLSA FF (composition %) | | | BA (composition %) | | | Blend of powders | |
|---|---|---|---|---|---|---|---|---|---|
| Ex. | Active ingredient | Formoterol | Leucine | Lactose | Tween 80 | Leucine | Lactose | Tween 80 | HLSA Bud (mg) | BA (mg) |
| 19 | formoterol | 2.25 | 0 | 97.25 | 0.5 | | | | 5 | 0 |
| 20 | formoterol | 2.25 | 20 | 77.25 | 0.5 | | | | 5 | 0 |
| 21 | formoterol | 2.25 | 97.25 | 0 | 0.5 | | | | 5 | 0 |
| 22 | formoterol | 2.25 | 0 | 97.25 | 0.5 | 0 | 99.5 | 0.5 | 0.01 | 9.99 |
| 23 | formoterol | 2.25 | 0 | 97.25 | 0.5 | 50 | 49.5 | 0.5 | 0.01 | 9.99 |
| 24 | formoterol | 2.25 | 0 | 97.25 | 0.5 | 99.5 | 0 | 0.5 | 0.01 | 9.99 |
| 25 | formoterol | 2.25 | 20 | 77.25 | 0.5 | 0 | 99.5 | 0.5 | 0.01 | 9.99 |
| 26 | formoterol | 2.25 | 20 | 77.25 | 0.5 | 50 | 49.5 | 0.5 | 0.01 | 9.99 |
| 27 | formoterol | 2.25 | 20 | 77.25 | 0.5 | 99.5 | 0 | 0.5 | 0.01 | 9.99 |
| 28 | formoterol | 2.25 | 97.25 | 0 | 0.5 | 0 | 99.5 | 0.5 | 0.01 | 9.99 |
| 29 | formoterol | 2.25 | 97.25 | 0 | 0.5 | 50 | 49.5 | 0.5 | 0.01 | 9.99 |
| 30 | formoterol | 2.25 | 97.25 | 0 | 0.5 | 99.5 | 0 | 0.5 | 0.01 | 9.99 |

TABLE 3B

| | Water content (%) | | Particle size (μm) | | % content of active ingredient | |
|---|---|---|---|---|---|---|
| Ex. | T0 | T3 | T0 | T3 | T0 | T3 |
| 19 | 4.2 | 3.6 | 2.5 | 2.85 | 96.6 | 97.4 |
| 20 | 3.3 | 3.3 | 1.5 | 1.33 | 100.3 | 95.3 |
| 21 | 0.8 | 0.6 | 2.6 | 2.59 | 95.2 | 89.3 |
| 22 | 2.8 | 1.7 | 3.4 | 3.98 | 98.8 | 90.5 |
| 23 | 3.2 | 2 | 2 | 2.12 | 98.5 | 97 |
| 24 | 0.7 | 0.3 | 3.3 | 3.59 | 95.5 | 86.1 |
| 25 | 2.6 | 1.8 | 3.1 | 3.88 | 97.2 | 88.9 |
| 26 | 2.4 | 1.7 | 2.1 | 2.16 | 96.8 | 101.5 |
| 27 | 0.6 | 0.4 | 2.8 | 3.52 | 92.7 | 76.5 |
| 28 | 2.6 | 2.3 | 3.3 | 3.82 | 78.7 | 73.2 |
| 29 | 2.4 | 1.8 | 2.1 | 2.17 | 84.6 | 87.8 |
| 30 | 0.4 | 0.2 | 3.2 | 3.52 | 93.6 | 68.8 |

TABLE 3C

| | Degradation (%) | | | DF (%) | | FPF (%) | |
|---|---|---|---|---|---|---|---|
| Ex. | T0 | T3 | Growth | T0 | T3 | T0 | T3 |
| 19 | 0.8 | 0.7 | 0.0 | 76.8 | 79.2 | 38.9 | 42.7 |
| 20 | 0.2 | 0.9 | 0.7 | 78.3 | 79.1 | 71.9 | 70.6 |
| 21 | 1.0 | 6.9 | 5.9 | 94.1 | 95.7 | 77.8 | 87.3 |
| 22 | 0.8 | 0.5 | 0.0 | 93.5 | 90.7 | 36.9 | 32.9 |
| 23 | 1.0 | 0.7 | 0.0 | 85.7 | 81.3 | 37.5 | 48.2 |
| 24 | 1.6 | 6.6 | 5 | 96.8 | 93.9 | 30.6 | 37.8 |
| 25 | 0.2 | 3.9 | 3.7 | 96.1 | 91.8 | 38 | 29.8 |
| 26 | 0.2 | 0.6 | 0.4 | 91.4 | 92.2 | 73.4 | 78.1 |
| 27 | 1.3 | 7.4 | 6.1 | 96.6 | 94 | 65.1 | 69.3 |
| 28 | 0.7 | 5.5 | 4.8 | 95 | 93 | 39.3 | 30.8 |
| 29 | 0.8 | 2.4 | 1.6 | 90.1 | 97.7 | 45.3 | 78.9 |
| 30 | 2.3 | 12.8 | 10.5 | 95.5 | 97.2 | 71.1 | 68.3 |

Example 4

The example was conducted comparing the products currently available on the market in different formulations with the mixture comprising the pharmaceutical composition according to the present invention containing variable amounts of budesonide and formoterol.

The product on the market used for the comparison was Symbicort®, manufactured by Astrazeneca, which is available in three different formulations, with a ratio of budesonide to formoterol fumarate expressed in μg of 320/9, 160/4.5 and 80/4.5.

The example was conducted to assess the aerosol performance of the composition according to the present invention. It is worth emphasizing that this composition can be administered at half the dose of the above-mentioned reference formulation currently on the market. This reduction of the dose having to be administered is achieved while:

- maintaining a high dose of drug delivery through the mouthpiece and a percentage of fine particles sufficient to guarantee that the quantity of drug deposited at the site of action can be pharmacologically effective;
- reducing the side-effects characteristic of the drugs being administered at the same time.

The powders in the composition according to the invention are as follows:

TABLE 4A

| Powder containing formoterol fumarate (HLSA FF) | |
|---|---|
| formoterol fumarate | 2.25% |
| leucine | 20.0% |
| lactose | 77.25% |
| Tween 80 | 0.5% |

TABLE 4B

| Powder containing budesonide (HLSA Bud) | |
|---|---|
| budesonide | 8.0% |
| leucine | 50.0% |
| lactose | 41.5% |
| Tween 80 | 0.5% |

TABLE 4C

| Bulking agent (BA) | |
|---|---|
| leucine | 50% |
| lactose | 49.5% |
| Tween 80 | 0.5% |

The three powders were blended together according to the previously-described methods to obtain three formulations containing budesonide and formoterol in a 10 mg or 3 mg dose of powder for comparison with the corresponding three reference formulations on the market (Tables 5 and 6).

TABLE 5

Composition of 10 mg formulations (budesonide/formoterol μg)

| | A1 (160/4.5) | A2 (80/2.25) | A3 (40/2.25) |
|---|---|---|---|
| HLSA FF | 2% | 1% | 1% |
| HLSA Bud | 20% | 10% | 5% |
| BA | 78% | 89% | 94% |

TABLE 6

Composition of 3 mg formulations (budesonide/formoterol μg)

| | B1 (160/4.5) | B2 (80/2.25) | B3 (40/2.25) |
|---|---|---|---|
| HLSA FF | 6.67% | 3.33% | 3.33% |
| HLSA Bud | 66.67% | 33.33% | 16.67% |
| BA | 26.66% | 63.34% | 80.00% |

The aerodynamic performance of the three formulations prepared as described (Table 5) was compared with that of the reference powders on the market using the MSLI and conducting the test at 4 kPa.

TABLE 7

| | DF (%) | FPF (%) | FPM < 5 μm (μg) | FPM < 3.5 μm (μg) | FPM < 2 μm (μg) | MMAD (μm) |
|---|---|---|---|---|---|---|
| FORMOTEROL | | | | | | |
| Symbicort 320/9 | 54.4 ± 7.8 | 60.2 ± 2.2 | 2.9 ± 0.4 | 2.6 ± 0.4 | 1.5 ± 0.2 | 2.1 ± 0.1 |
| A1 160-4.5 | 88.9 ± 2.2 | 80.0 ± 2.2 | 3.2 ± 0.1 | 2.7 ± 0.1 | 1.4 ± 0.1 | 2.3 ± 0.1 |
| B1 160-4.5 | 80.6 ± 4.7 | 82.2 ± 1.0 | 3.0 ± 0.1 | 2.7 ± 0.1 | 1.4 ± 0.1 | 2.1 ± 0.0 |
| BUDESONIDE | | | | | | |
| Symbicort 320/9 | 53.8 ± 8.8 | 57.2 ± 3.2 | 98.4 ± 17.2 | 85.7 ± 14.3 | 46.9 ± 7.2 | 2.2 ± 0.1 |
| A1 160-4.5 | 92.1 ± 1.4 | 76.9 ± 2.4 | 113.2 ± 3.7 | 93.8 ± 3.6 | 48.3 ± 2.4 | 2.4 ± 0.1 |
| B1 160-4.5 | 92.3 ± 3.4 | 79.7 ± 1.8 | 120.1 ± 4.3 | 107.8 ± 4.3 | 65.0 ± 3.8 | 2.0 ± 0.0 |

Table 7 compares the formulations A1 and B1 described in Tables 6 and 7 (dosage 160/4.5; 96 L/min-2.5 s) with Symbicort® 320/9 (dosage 320/9; 58 L/min-4.1 s).

TABLE 8

|  | DF (%) | FPF (%) | FPM < 5 μm (μg) | FPM < 3.5 μm (μg) | FPM < 2 μm (μg) | MMAD (μm) |
|---|---|---|---|---|---|---|
| FORMOTEROL | | | | | | |
| Symbicort 160/4.5 | 66.7 ± 13.3 | 52.7 ± 4.1 | 1.6 ± 0.4 | 1.4 ± 0.3 | 0.7 ± 0.2 | 2.4 ± 0.1 |
| A2 80-2.25 | 88.9 ± 4.4 | 83.0 ± 2.2 | 1.7 ± 0.0 | 1.4 ± 0.1 | 0.8 ± 0.1 | 2.2 ± 0.1 |
| B2 80-2.25 | 89.7 ± 5.6 | 83.3 ± 1.1 | 1.7 ± 0.0 | 1.5 ± 0.0 | 0.9 ± 0.0 | 2.0 ± 0.0 |
| BUDESONIDE | | | | | | |
| Symbicort 160/4.5 | 73.7 ± 14.3 | 54.8 ± 2.7 | 64.8 ± 14.2 | 55.7 ± 11.8 | 30.8 ± 6.2 | 2.3 ± 0.1 |
| A2 80-2.25 | 96.4 ± 2.3 | 80.9 ± 2.1 | 62.4 ± 1.9 | 53.2 ± 2.0 | 29.6 ± 2.1 | 2.2 ± 0.1 |
| B2 80-2.25 | 100.6 ± 7.2 | 80.1 ± 1.8 | 62.8 ± 1.8 | 56.6 ± 1.6 | 35.3 ± 0.7 | 1.9 ± 0.1 |

Table 8 compares the formulations A2 and B2 described in Tables 5 and 6 (dosage 80/2.25; 96 L/min-2.5 s) with Symbicort® 160/4.5 (dosage 160/4.5; 58 L/min-4.1 s).

TABLE 9

|  | DF (%) | FPF (%) | FPM < 5 mm (μg) | FPM < 3.5 mm (μg) | FPM < 2 mm (μg) | MMAD (μm) |
|---|---|---|---|---|---|---|
| FORMOTEROL | | | | | | |
| Symbicort 80/4.5 | 60.0 ± 8.9 | 60.4 ± 3.1 | 1.6 ± 0.2 | 1.4 ± 0.2 | 0.8 ± 0.1 | 2.2 ± 0.1 |
| A3 40-2.25 | 88.9 ± 0.0 | 82.4 ± 1.3 | 1.7 ± 0.0 | 1.4 ± 0.1 | 0.7 ± 0.1 | 2.3 ± 0.1 |
| B3 40-2.25 | 84.5 ± 3.0 | 82.6 ± 0.9 | 1.6 ± 0.0 | 1.4 ± 0.0 | 0.8 ± 0.0 | 2.1 ± 0.1 |
| BUDESONIDE | | | | | | |
| Symbicort 80/4.5 | 63.9 ± 9.1 | 61.4 ± 2.3 | 31.3 ± 4.4 | 27.6 ± 3.9 | 16.0 ± 1.9 | 2.1 ± 0.0 |
| A3 40-2.25 | 94.5 ± 1.8 | 80.7 ± 1.9 | 30.5 ± 0.9 | 25.8 ± 1.1 | 13.9 ± 1.2 | 2.3 ± 0.1 |
| B3 40-2.25 | 94.0 ± 2.9 | 81.5 ± 0.9 | 30.2 ± 0.2 | 27.1 ± 0.1 | 16.2 ± 0.2 | 2.0 ± 0.0 |

Table 9 compares the formulations A3 and B3 described in Tables 5 and 6 (dosage 40/2.25; 96 L/min-2.5 s) with Symbicort® 80/4.5 (dosage 80/4.5; 58 L/min-4.1 s).

The invention claimed is:

1. A pharmaceutical composition for inhalatory use which is obtained by preparing:
   a) a first powder comprising budesonide or a pharmaceutically acceptable salt thereof, if in an amount greater than 5% by weight of said first powder, leucine in an amount from 18 to 55% by weight of said first powder, lactose in an amount from 40 to 80% by weight of said first powder;
   b) a second powder comprising formoterol or a pharmaceutically acceptable salt thereof, in an amount greater than 1% by weight of said second powder, leucine in an amount from 18 to 55% by weigh t of said second powder, lactose in an amount from 40 to 80% by weight of said second powder;
   c) a third powder comprising leucine in an amount from 18 to 55% by weight of said third powder and lactose in an amount from 40 to 80% by weight of said third powder; and
   d) blending said first, second and third powders to form a single mixture;

wherein said first powder is in an amount from 5 to 67% and said second powder is in an amount from 1 to 7% with respect to the total amount of the composition, the remaining balance of the total amount of the composition being said third powder; and said composition has a fine particle fraction (FPF) greater than 60% and an delivered fraction (DF) greater than 90%.

2. The composition according to claim 1, wherein said first and second powder comprise a surfactant in an amount from 0.2 to 2% by weight of each powder.

3. The composition according to claim 1, wherein the budesonide in an amount greater than 7% by weight of said first powder.

4. The composition according to claim 1, wherein said formoterol is in an amount greater than 2% by weight of said second powder.

5. The composition according to claim 2, wherein said surfactant is selected from the group consisting of: benzalkonium chloride, cetrimide, docusate sodium, glyceryl monooleate, sorbitan esters, sodium lauryl sulfate, polysorbates, phospholipids, bile salts, block copolymers of polyoxyethylene and polyoxypropylene.

6. The composition according to claim 2, wherein said surfactant is in an amount from 0.4 to 0.8% by weight of the composition.

7. The composition according to claim 1, wherein said first, second and third powder have a X50 less than 5 μm.

8. The composition according to claim 1, wherein the budesonide is in an amount from 35 to 45 μg and the formoterol is in an amount from 1.5 to 3 μg per inhalatory unit dose.

9. The composition according to claim 1, wherein the budesonide is in an amount from 75 to 85 μg and the formoterol is in an amount from 1.5 to 3 μg per inhalatory unit dose.

10. The composition according to claim 1, wherein the budesonide is in an amount from 155 to 165 μg and the formoterol is in an amount from 4 to 5 μg per inhalatory unit dose.

11. The composition according to claim 1 for use in the treatment of asthma both maintenance and need therapy.

12. The composition according to claim 1 for use in the treatment of chronic obstructive pulmonary disease.

13. A kit for the administration of a drug as inhalatory powder, comprising a metered amount of the composition according to claim 1 and a device for inhalation.

14. The composition according to claim 2, wherein the budesonide in an amount greater than 7% by weight of said first powder.

15. The composition according to claim 1, wherein for a total amount of the composition in the range of 3 to 10 mg, said first powder is in an amount from 5 to 67% and said second powder is in an amount from 1 to 7% and the remaining balance of the total amount of the composition being said third powder which is in an amount from 26 to 94%.

16. The composition according to claim 1, wherein for a total amount of the composition of 10 mg, said first powder is in an amount from 5 to 20% and said second powder is in an amount from 1 to 2% and the remaining balance of the total amount of the composition being said third powder which is in an amount from 78 to 94%.

17. The composition according to claim 1, wherein for a total amount of the composition of 3 mg, said first powder is in an amount from 16 to 67% and said second powder is in an amount from 3 to 7% and the remaining balance of the total amount of the composition being said third powder which is in an amount from 26 to 80%.

18. The composition according to claim 1, wherein the molar ratio of the budesonide and formoterol is from 15:1 to 40:1.

19. The composition according to claim 1, wherein the budesonide is in an amount from 30 to 180 μg and the formoterol is in an amount from 1.5 to 5.5 μg per inhalatory unit dose, which is the inhalatory dose that is emitted from the mouthpiece of the inhaler after each inhalation.

* * * * *